US008703471B2

(12) United States Patent
Aebi et al.

(10) Patent No.: US 8,703,471 B2
(45) Date of Patent: *Apr. 22, 2014

(54) SYSTEM AND METHOD FOR THE PRODUCTION OF RECOMBINANT GLYCOSYLATED PROTEINS IN A PROKARYOTIC HOST (75) Inventors: Markus Aebi, Wettingen (CH); Michael Wacker, Unterengstringen (CH)

(73) Assignee: ETH Zürich, Zürich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/219,383

(22) Filed: Jul. 21, 2008

(65) Prior Publication Data

US 2009/0074798 A1 Mar. 19, 2009

Related U.S. Application Data (63) Continuation of application No. 10/506,917, filed as application No. PCT/CH03/00153 on Mar. 5, 2003, now abandoned.

(60) Provisional application No. 60/364,655, filed on Mar. 14, 2002.

(30) Foreign Application Priority Data

Mar. 7, 2002 (CH) ........................ 0394/02

(51) Int. Cl.
| C12N 1/20 | (2006.01) |
| C12N 15/00 | (2006.01) |
| C12N 9/10 | (2006.01) |
| C12P 21/06 | (2006.01) |
| C12P 21/04 | (2006.01) |
| C07H 21/04 | (2006.01) |
| C07H 21/02 | (2006.01) |
| C07K 1/00 | (2006.01) |
| A61K 38/00 | (2006.01) |

(52) U.S. Cl.
USPC ............... 435/252.3; 435/193; 435/320.1; 435/252.33; 435/69.1; 435/71.1; 536/23.2; 536/23.1; 530/324; 530/350

(58) Field of Classification Search
None
See application file for complete search history.

(56) References Cited

U.S. PATENT DOCUMENTS

| 5,643,758 A | 7/1997 | Guan et al. |
| 2002/0019342 A1 | 2/2002 | Bayer |
| 2004/0265954 A1 | 12/2004 | Aebi et al. |
| 2005/0287628 A1 | 12/2005 | Aebi et al. |

FOREIGN PATENT DOCUMENTS

| CA | 1340184 | 12/1998 |
| CA | 2 360 205 | 8/2000 |
| CA | 2 477 794 | 3/2003 |
| EP | 1 481 057 | 2/2006 |
| WO | WO-94/26906 | 11/1994 |
| WO | WO-00/52135 | 9/2000 |
| WO | WO-01/88117 | 11/2001 |
| WO | WO-02/00856 | 1/2002 |
| WO | WO-03/074687 | 9/2003 |
| WO | WO-2004/013151 A2 | 2/2004 |
| WO | WO-2005/116063 A1 | 12/2005 |
| WO | WO-2006/119987 A2 | 11/2006 |
| WO | WO-2009/104074 A2 | 8/2009 |

OTHER PUBLICATIONS

Branden et al. Introduction to Protein Structure, Garland Publishing Inc., New York, p. 247, 1991.*
Yao et al. Isolation of motile and non-motile insertional mutants of *Campylobacter jejuni*: the role of motility in adherence and invasion of eukaryotic cells. Mol Microbiol. Dec. 1994;14(5):883-93.*
Kuwajima et al. Nucleotide sequence of the hag gene encoding flagellin of *Escherichia coli*. J Bacteriol. Dec. 1986;168(3):1479-83.*
Alaimo, C. et al., "Two distinct but interchangeable mechanisms for flipping of lipid-linked oligosaccharides," EMBO Journal 25, pp. 967-976 (2006).
Baneyx, F., "Recombinant protein expression in *Escherichia coli*," Curr. Opin. Biotechnol. 10, pp. 411-421 (1999).
Berg, A. and de Kok, A., "2-Oxo Acid Dehydrogenase Multienzyme Complexes: The Central Role of the Lipoyl Domain," Bioliology Chemistry, 378, pp. 617-634 (1997).
Bill, R.M. et al., "Expression and mutagenesis of recombinant human and murine erythropoietins in *Escherichia coli*," Biochimica et Biophysica Acta 1261, pp. 35-43 (1995).
Billman-Jacobe, H., "Expression in bacteria other than *Escherichia coli*," Curr. Opin. Biotechnol. 7, pp. 500-504 (1996).
Bugg, T.D. and Brandish, P.E., "From peptidoglycan to glycoproteins: Common features of lipid-linked oligosaccharide biosynthesis," FEMS Microbiol. Lett. 119, pp. 255-262 (1994).

(Continued)

*Primary Examiner* — Yong Pak
(74) *Attorney, Agent, or Firm* — Jones Day (57) ABSTRACT A system and a method for the production of recombinant N-glycosylated target proteins. The system comprises a prokaryotic organism (e.g. *Escherichia coli*) into which is introduced a genetic information encoding for a metabolic apparatus capable of carrying out the requested N-glycosylation of the target protein. Said prokaryotic organism also contains the genetic information required for the expression of one or more recombinant target proteins. The metabolic apparatus preferably comprises specific glycosyltransferases for the assembly of the oligosaccharide on a lipid carrier and an OTase that covalently links this oligosaccharide to specific residues of the desired protein.

7 Claims, 2 Drawing Sheets

(56) References Cited

OTHER PUBLICATIONS

Choi, J.H. and Lee, S.Y., "Secretory and extracellular production of recombinant proteins using *Escherichia coli*," Appl. Microbiol. Biotechnol. 64, pp. 625-635 (2004).

Feldman et al., "Engineering N-linked protein glycosylation with diverse O antigen lipopolysaccharide structures in *Escherichia coli*," Proc. Natl. Acad. Sci. USA 102, pp. 3016-3021 (2005).

Francisco, J.A. et al., "Transport and anchoring of β-lactamase to the external surface of *Escherichia coli*," Proc. Natl. Acad. Sci. USA 89: 2713-2717 (1992).

Glover, K.J. et al., "Chemoenzymatic Synthesis of Glycopeptides with PgIB, a Bacterial Oligosaccharyl Transferase from *Campylobacter jejuni*," Chemistry & Biology, vol. 12, pp. 1311-1316 (2005).

Helenius, A. and Aebi, M., "Roles of N-linked Glycans in the Endoplasmic Reticulum," Annu. Rev. Biochem. 73, pp. 1019-1049 (2004).

Higgins et al., "Structure of the periplasmic component of a bacterial drug efflux pump," Proc. Natl. Acad. Sci. USA 101, pp. 9994-9999 (2004).

Hoiseth, S.K. and Stocker, B.A., "Aromatic-dependent *Salmonella typhimurium* are non-virulent and effective as live vaccines," Nature 291: 238-239 (1981).

Imperiali, B. and Shannon, K.L., "Differences between Asn-Xaa-Thr-containing peptides: a comparison of solution conformation and substrate behaviour with oligosaccharyl-transferase," Biochemistry 30, pp. 4374-4380 (1991).

Jeong, K.J. and Lee S.Y., "Secretory Production of Human Granulocyte Colony-Stimulating Factor in *Escherichia coli*," Protein Expression and Purification 23, pp. 311-318 (2001).

Johnson, J.M. and Church, G.M., "Alignment and Structure Prediction of Divergent Protein Families: Periplasmic and Outer Membrane Proteins of Bacterial Efflux Pumps," J. Mol. Biol. 287, pp. 695-715 (1999).

Kaniuk, N.A. et al., "Investigation of the Structural Requirements in the Lipopolysaccharide Core Acceptor for Ligation of O Antigens in the Genus *Salmonella*: WaaL 'Ligase' Is Not the Sole Determinant of Acceptor Specificity," J. Biological Chemistry 279: 36470-36480 (2004).

Muller, A. et al., "An ATP-binding cassette-type cysteine transporter in *Campylobacter jejuni* inferred from the structure of an extracytoplasmic solute receptor protein," Mol. Microbiol. 57: 143-155 (2005).

Paetzel, M. et al., "Signal Peptidases," Chem. Rev. 102: 4549-4580 (2002).

Petrescu et al., "Statistical analysis of the protein environment of *N*-glycosylation sites: implications for occupancy, structure, and folding," Glycobiology, vol. 14, No. 2 pp. 103-114, 2004.

Rudd, P.M. and Dwek, R.A., "Glycosylation: Heterogeneity and the 3D Structure of Proteins," Crit. Rev. Biochem. Mol. Biol. 32, pp. 1-100 (1997).

Schulz, H. et al., "Prototype of a Heme Chaperone Essential for Cytochrome c Maturation," Science 281, pp. 1197-1200 (1998).

Simons, G. et al., "High-level expression of human interferon gamma in *Escherichia coli* under control of the $p_L$ promoter of bacteriophage lambda," Gene 28, pp. 55-64 (1984).

Valvano, M.A., "Export of O-Specific Lipopolysaccharide," Front. Biosci. 8, s452-471 (2003).

Wacker, et al., "Substrate specificity of bacterial oligosaccharyltransferase suggests a common transfer mechanism for the bacterial and eukaryotic systems," Proc. Natl. Acad. Sci. 103, pp. 7088-7093 (2006).

Wernerus, H. and Stahl, S. "Biotechnological applications for surface-engineered bacteria," Biotechnol. Appl. Biochem. 40: 209-228 (2004).

Wyszynska, A. et al., "Oral immunization of chickens with avirulent *Salmonella* vaccine strain carrying *C. jejuni* 72Dz/92 cjaA gene elicits specific humoral immune response associated with protection against challenge with wild-type *Campylobacter*," Vaccine 22, pp. 1379-1389 (2004).

Ahmed, A. et al., "Safety and Immunogenicity of *Escherichia coli* O157 O-Specific Polysaccharide Conjugate Vaccine in 2-5—Year Old Children," Journal of Infectious Diseases, vol. 193, No. 4, pp. 515-521 (Feb. 15, 2006) (elec. pub. Jan. 13, 2006).

Anderson, P., "Antibody Responses to *Haemophilus influenzae* Type b and Diphtheria Toxin Induced by Conjugates of Oligosaccharides of the Type b Capsule with the Nontoxic Protein $CRM_{197}$," Infection and Immunity, vol. 39, No. 1, pp. 233-238 (Jan. 1983).

Baqar, S. et al., "Safety and immunogenicity of a prototype oral whole-cell killed *Campylobacter* vaccine administered with a mucosal adjuvant in non-human primates," Vaccine, vol. 13, No. 1, pp. 22-28 (Jan. 1995).

Burr, D.H. et al., "Prevention of disease in ferrets fed an inactivated whole cell *Campylobacter jejuni* vaccine," Vaccine, vol. 23, pp. 4315-4321 (Jul. 29, 2005) (available online May 3, 2005).

Butzler, J.P., "*Campylobacter*, from obscurity to celebrity," Clinical Microbiology and Infection, pp. 868-876 (Oct. 2004).

Casburn-Jones, A.C. et al., "Traveler's diarrhea," Journal of Gastroenterology and Hepatology, vol. 19, pp. 610-618 (Jun. 2004).

Chart, H. et al., "Serological identification of *Escherichia coli* O157:H7 infection in haemolytic uraemic syndrome," The Lancet, vol. 337, pp. 138-140 (Jan. 19, 1991).

Chemistry and Biology, vol. 39, No. 10, pp. 632-634 (2001).

Crushell, E. et al., "Enteric *Campylobacter*. Purging Its Secrets?" Pediatric Research, vol. 55, No. 1, pp. 3-12 (Jan. 2004).

Doig et al., "Characterization of a post-translational modification of *Campylobacter flagellin*: identification of a sero-specific glycosyl moiety," Molecular Microbiology, Vo. 19, No. 2, pp. 379-387 (1996).

Fairweather, N. F. et al., "Cloning, Nucleotide Sequencing, and Expression of Tetanus Toxin Fragment C in *Escherichia coli*," Journal of Bacteriology, vol. 165, No. 1, pp. 21-27 (Jan. 1986).

Fass, R. et al., "Use of high density cultures of *Escherichia coli* for high level production of recombinant *Pseudomonas aeruginosa* exotoxin A," Applied Microbiology and Biotechnology, vol. 36, No. 1, pp. 65-69 (Oct. 1991).

Fattom A. et al., "Laboratory and Clinical Evaluation of Conjugate Vaccines Composed of *Staphylococcus aureus* Type 5 and Type 8 Capsular Polysaccharides Bound to *Pseudomonas aeruginosa* Recombinant Exoprotein A," Infection and Immunity, vol. 61, No. 3, pp. 1023-1032 (Mar. 1993).

Goebel, W.F. and Avery, O.T., "Chemo-Immunological Studies on Conjugated Carbohydrate-Proteins," Journal of Experimental Medicine, pp. 521-531 (1929).

Guerry et al., "Identification and characterization of genes required for post-translational modification of *Campylobacter coli* VC167 flagellin," Moleclar Microbiology, vol. 19, No. 2, pp. 369-378 (1996).

Haberberger, R.L. et al., "Prospects and Problems for Development of a Vaccine against Diarrhea Caused by *Campylobacter*," Vaccine Research, vol. 3, pp. 15-22 (Nov. 1, 1994).

Karlyshev, A.V. et al., "The *Campylobacter jejuni* general glycosylation system is important for attachment to human epithelial cells and in the colonization of chicks," Microbiology, vol. 150, pp. 1957-1964 (Jun. 2004).

Konadu, E. et al., "Investigational Vaccine for *Escherichia coli* O157: Phase 1 Study of O157 O-Specific Polysaccharide-*Pseudomonas aeruginosa* Recombinant Exoprotein A Conjugates in Adults, Journal of Infectious Diseases," vol. 177, No. 2, pp. 383-387 (Feb. 1998).

Konadu, E. et al., "Preparation, Characterization, and Immunological Properties in Mice of *Escherichia coli* O157 O-Specific Polysaccharide—Protein Conjugate Vaccines," Infection and Immunity, vol. 62, No. 11, pp. 5048-5054 (Nov. 1994).

Konadu, E. et al., "Syntheses and Immunologic Properties of *Escherichia coli* O157 O-Specific Polysaccharide and Shiga Toxin 1 B Subunit Conjugates in Mice," Infection and Imiunnity, vol. 67, No. 11, pp. 6191-6193 (Nov. 1999).

Kowarik, M. et al., "N-Linked Glycosylation of Folded Proteins by the Bacterial Oligosaccharyltransferase," Science, vol. 314, pp. 1148-1150 (Nov. 17, 2006).

(56) References Cited

OTHER PUBLICATIONS

Lee, L.H. et al., "Evaluation of a Truncated Recombinant Flagellin Subunit Vaccine against *Campylobacter jejuni*," Infection and Immunity, vol. 67, No. 11, pp. 5799-5805 (Nov. 1999).
Linton D. et al., "Functional analysis of the *Campylobacter jejuni* N-linked protein glycosylation pathway," Molecular Microbiology, vol. 55, No. 6, pp. 1695-1703 (Mar. 2005).
Lukac, M. et al., "Toxoid of *Pseudomonas aeruginosa* Exotoxin A Generated by Deletion of an Active-Site Residue," Infection and Immunity, vol. 56, No. 12, pp. 3095-3098 (Dec. 1988).
Middlebrook, J.L. et al., "Bacterial Toxins: Cellular Mechanisms of Action," Microbiological Reviews, vol. 48, No. 3, pp. 199-221 (Sep. 1984).
Nairn, J.G., "Solutions, Emulsions, Suspensions and Extracts," Remington's Pharmaceutical Sciences, 18th ed., Mack Publishing Co., Chapter 83, pp. 1519-1544 (1990).
Panina-Bordignon, P. et al., "Universally immunogenic T cell epitopes: promiscuous binding to human MHC class II and promiscuous recognition by T cells*," European Journal of Immunology, vol. 19, pp. 2237-2242 (Dec. 1989).
Parkhill, J. et al., "The genome sequence of the food-borne pathogen *Campylobacter jejuni* reveals hypervariable sequences," Nature, vol. 403, pp. 665-668 (Feb. 10, 2000).
Passwell, J.H. et al., "Safety and Immunogenicity of Improved *Shegella* O-Specific Polysaccharide-Protein Conjugate Vaccines in Adults in Israel," Infection and Immunity, vol. 69, No. 3, pp. 1351-1357 (Mar. 2001).
Pearson, B.M. et al., "Comparative genome analysis of *Campylobacter jejuni* using whole genome DNA microarrays," FEBS Letter, vol. 554, FEBS 27782, pp. 224-230 (Nov. 6, 2003) (pub. online Oct. 16, 2003).
Pozsgay, V. et al., "Protein conjugates of synthetic saccharides elicit higher levels of serum IgG lipopolysaccharide antibodies in mice than do those of the O-specific polysaccharide from *Shigella dysenteriae* type 1," Proceedings of the National Academy of Sciences, vol. 96, pp. 5194-5197 (Apr. 27, 1999).
Pozsgay, V., "Synthesis of Glycoconjugate Vaccines again *Shigella dysenteriae* Type 1," Journal of Organic Chemistry, vol. 63, pp. 5983-5999 (Aug. 21, 1998) (pub. on web Jul. 29, 1998).
Raetz & Whitfield, "Lipopolysaccharide Endotoxins," *NIH-PA Author Manuscript*, pp. 1-57 (published in final edited form as: *Annual Rev. Biochem.*, 71:635-700 (2002) (Epub Nov. 9, 2001)).
Reeves et al., "Bacterial polysaccharide synthesis and gene nomenclature," Reviews, Elseview Science Ltd., pp. 495-503 (1996).
Schaad, U.B. et al., "Safety and immunogenicity of *Pseudomonas aeruginosa* conjugate A vaccine in cystic fibrosis," The Lancet, vol. 338, pp. 1236-1237 (Nov. 16, 1991).
Schneerson, R. et al., Preparation, Characterization, and Immunogenicity of *Haemophilus influenzae* Type b Polysaccharide-Proteins Conjugates, Journal of Experimental Medicine, vol. 152, pp. 361-376 (Aug. 1, 1980).
Scott, D.A., "Vaccines against *Campylobacter jejuni*," Journal of Infectious Diseases, vol. 176, Suppl. 2, S183-S188 (Dec. 1997).
Szu, S.C. et al., "Laboratory and Preliminary Clinical Characterization of Vi Capsular Polysaccharide-Protein Conjugate Vaccines," Infection and Immunity, vol. 62, No. 10, pp. 4440-4444 (Oct. 1994).
Szymanski, C.M. et al. "Protein Glycosylation in Bacterial Mucosal Pathogens," Nature Reviews, Microbiology, vol. 3, pp. 225-237 (Mar. 2005) (pub. online Feb. 10, 2005).
Szymanski, C.M. et al., "*Campylobacter* Protein Glycosylation Affects Host Cell Interactions," Infection and Immunity, vol. 70, No. 4, pp. 2242-2244 (Apr. 2002).
Taylor, D.N. et al., "Synthesis, Characterization, and Clinical Evaluation of Conjugate Vaccines Composed of the O-Specific Polysaccharides of *Shigella dysenteriae* Type 1, *Shigella flexneri* Type 2a, and *Shigella sonnei* (*Plesiomonas shigelloides*) Bound to Bacterial Toxoids," Infection and Immunity, vol. 61, No. 9, pp. 3678-3687 (Sep. 1993).

Thibault et al., "Identification of the Carbohydrate Moieties and Glycosylation Motifs in *Campylobactor jejuni* Flagellin," The Journal of Biological Chemistry, vol. 276, No. 37, pp. 34862-34870 (Sep. 2001).
Whitfield et al., Structure, assembly and regulation of express of capsules in *Escherichia coli*, Molecular Microbiology, vol. 31, No. 5, pp. 1307-1319 (1999).
Kowarik, Michael et al., "Definition of the bacterial N-glycosylation site consensus sequence" EMBO (European Molecular Biology Organization) Journal, vol. 25, No. 9, May 2006, pp. 1957-1966, XP002408605, ISSN: 0261-4189.
Nita-Lazar, Mihai et al., "The N-X-S/T consensus sequence is required but not sufficient for bacterial N-linked protein glycosylation" Glycobiology, vol. 15, No. 4, Apr. 2005, pp. 361-367, XP002408606, ISSN: 0959-6658.
Linton, D. et al., "Identification of N-acetylgalactosamine-containing glycoproteins PEB3 and CgpA in *Campylobacter jejuni*" Molecular Microbiology, Blackwell Scientific, Oxford, GB, vol. 43, No. 2, 2002, pp. 497-508, XP002267530.
Crooks, Gavin E. et al., "WebLogo: A sequence logo generator" Genome Research, vol. 14, No. 6, Jun. 2004, pp. 1188-1190, XP002408756, ISSN: 1088-9051.
Altmann et al., "Insect cells as hosts for the expression of recombinant glycoproteins" Glycoconjugate Journal, 16, p. 109-23 (1999).
Fujita et al., "Synthesis of Neoglycoenzymes with Homogenous N-Linked Oligosaccharides Using Immobilized Endo-S-N-acetylglucosaminidase A" Biochemical and Biophysical Research Communications, 267, p. 134-38 (2000).
Gavel et al., "Sequence differences between glycosylated and non-glycosylated and non-glycosylated Asn-X-Thr/Ser acceptor sites: implications for protein engineering" Protein Eng, 3, p. 433-42 (1990).
Grabenhorst et al., "Genetic engineering of recombinant glycoproteins and the glycosylation pathway in mammalian host cells" Glycoconjugate Journal, 16, p. 81-97 (1999).
Malissard et al., "The yeast expression system for recombinant glycosyltransferases" Glycoconjugate Journal, 16, p. 125-39 (1999).
Maras, et al., "Filamentous fungi as production organisms for glycoproteins of bio-medical interest" Glycoconjugate Journal, 16, p. 99-107 (1999).
Fry et al., "The lipopolysaccharide biosynthesis locus of *Campylobacter jejuni* 81116" Microbiology, vol. 144, p. 2049-61 (1998).
Burda et al., "The dolichol pathway of N-linked glycosylation" Biochimica et Biophysica Acta, 1426, p. 239-57 (1999).
Szymanski et al., "Evidence for a system of general protein glyscosylation in *Campylobacter jejuni*" Molecular Microbiology, vol. 32, Issue 5, p. 1022-30 (Jun. 1999).
Young et al., "Structure of the N-Linked Glycan Present on Mulitple Glycoproteins in the Gramnegative Bacterium, *Campylobacter jujuni*" The Journal of Biological Chemistry, vol. 277, No. 45, p. 42530-39 (Nov. 2002).
Wacker et al., "N-Linked Glycosylation in *Campylobacter jejuni* and Its Functional Transfer into *E. coli*" Science, vol. 298, p. 1790-93 (Nov. 2002).
Wacker et al., "PglB, an oligosaccharyltransferase in the eubacterium *Campylobacter jejuni*?" Glycobiology, vol. 11, p. 871 (Oct. 2001).
Varki et al., Essential of Glycobiology, Cold Spring Harbor Laboratory Press, Cold Spring Harbor, New York, 1999.
Grabenhorst et al., "Genetic engineering of recombinant glycoproteins and the glycosylation pathway in mannalian host cells" Glycoconjugate Journal, 16, p. 81-97 (1999).
Altmann et al., "Insects cells as host for the express system for recombinant glycoproteins" Glycoconjugate Journal, 16, p. 109-123 (1999).
Abdian, P.L. et al., Identification of Essential Amino Acids in the Bacterial α- Mannosyltransferase AceA, *J. Biol. Chem.* 275(51): 40568-40575 (Sep. 21, 2000).
Aebi, M., et al., Cloning and characterization fo the ALG3 gene of *Saccharomyces cerevisiae*, Glycobiology 6, pp. 439-444 (1996).

(56) References Cited

OTHER PUBLICATIONS

Alexander, D., et al., Role of the *rfe* Gene in the Biosynthesis of the *Escherichia coli* O7-Specific Lipopolysaccharide and Other O-Specific Polysaccharides Containing N-Acetylglucosamine, J. Bacteriol. 176, pp. 7079-7084 (1994).

Allard, S.T., et al., Epimerases: structure, function and mechanism, Cell. Mol. Life Sci. 58, pp. 1650-1665 (2001).

Amor, P.A., et al., Molecular and functional analysis of genes required for expression of group IB K antigens in *Escherichia coli*: characterization of the *his*-region containing gene clusters for multiple cell-surface polysaccharides, Mol. Microbiol. 26, pp. 145-161 (1997).

Arbeit, R. D., W. W. Karakawa, W. F. Vann, and J. B. Robbins. 1984. Predominance of two newly described capsular polysaccharide types among clinical isolates of *Staphylococcus aureus*. Diagn Microbiol Infect Dis 2:85-91.

Avery, O. T., and W. F. Goebel. 1929. Chemo-immunological studies on conjugated carbohydrate-proteins. II Immunological specificity of synthetic sugar-proteins. J. Exp. Med. 50:521-531.

Baggett, H. C., T. W. Hennessy, K. Rudolph, D. Bruden, A. Reasonover, A. Parkinson, R. Sparks, R. M. Donlan, P. Martinez, K. Mongkolrattanothai, and J. C. Butler. 2004. Community-onset methicillin-resistant *Staphylococcus aureus* associated with antibiotic use and the cytotoxin Panton-Valentine leukocidin during a furunculosis outbreak in rural Alaska. J Infect Dis 189:1565-73.

Berg, S. et al., Sequence Properties of the 1,2-Diacylglycerol 3-Glucosyltransferase from *Acholepasma laidlawii* Membranes, *J. Bio. Chem*. 276(25): 22056-22063 (Apr. 6, 2001).

Bernatchez, S., et al., A Single Bifunctional UDP-GlcNAc/Glc 4-Epimerase Supports the Synthesis of Three Cell Surface Glycoconjugates in *Campylobacter jejuni*\* J. Biol. Chem. 280, pp. 4792-4802 (2005).

Bhasin, N., A. Albus, F. Michon, P. J. Livolsi, J.-S. Park, and J. C. Lee. 1998. Identification of a gene essential for O-acetylation of the *Staphylococcus aureus* type 5 capsular polysaccharide. Mol Microbiol 27:9-21.

Bigge, J. C., T. P. Patel, J. A. Bruce, P. N. Goulding, S. M. Charles, R. B. Parekh. 1995. Nonselective and efficient fluorescent labeling of glycans using 2-amino benzamide and anthranilic acid. Anal Biochem 230(2): 229-38.

Bligh, E. G. and W. J. Dyer. 1959. A rapid method of total lipid extraction and purification. Can J Biochem Physiol 37(8): 911-917.

Bourne, Y. et al., Glycoside hydrolases and glycosyltransferases: families and functional modules, *Current Opinion in Structural Biology* 11:593-600 (2001).

Breton, C. & Imberty, A., Structure/function studies of glycosyltransferases, *Curr. Op. Struct. Bio*. 9: 563-571 (1999).

Bubeck Wardenburg, J., A. M. Palazzolo-Ballance, M. Otto, O. Schneewind, and F. R. DeLeo. 2008. Panton-Valentine leukocidin is not a virulence determinant in murine models of community-associated methicillin-resistant *Staphylococcus aureus* disease. J Infect Dis 198:1166-70.

Campbell, J. et al., A classification of nucleotide-diphospho-sugar glycosyltransferases based on amino acid sequence similarities, *Biochem. J*. 326: 929-939 (1997).

Canals, R. et al., The UDP N-Acetylgalactosamine 4-Epimerase Gene is Essential for Mesophilic *Aeromaonas hydrophila* Serotype O34 Virulence, *Infect. & Immun*. 74(1):537-548 (Jan. 2006).

Cardini, C.E., et al., Enzymatic Formation of Acetylgalactosamine J. Biol. Chem. 225, pp. 317-324 (1957).

CAZy (Carbohydrate-Active enZYmes) Database—Glycosyt-Transferase family Classification (AFMB—CNRS—Universités Aix-Marseille I & II) last update: Oct. 25, 2010 at http://www.cazy.org/GlycosylTransferases.html.

CAZy (Carbohydrate-Active enZYmes) Database—Home (AFMB—CNRS—Universités Aix-Marseille I & II) last update: Oct. 25, 2010 at http://www.cazy.org.

Chang, S., D. M. Sievert, J. C. Hageman, M. L. Boulton, F. C. Tenover, F. P. Downes, S. Shah, J. T. Rudrik, G. R. Pupp, W. J. Brown, D. Cardo, and S. K. Fridkin. 2003. Infection with vancomycin-resistant *Staphylococcus aureus* containing the *vanA* resistance gene. New Engl J Med 348:1342-7.

Consortium for Functional Glycomics (CFG) Nature, Functional Glycomics Gateway-Nomenclature, last update: Apr. 28, 2010 at http://www.functionalglycomics.org/static/consortium/Nomenclature.shtml.

Coutinho, P.M. & Henrissat, B., Life with No Sugars?, *J. Mol. Microbio. Biotech*. 1(2): 307-308 (1999).

Cruezenet, C. et al., Expression, Purification, and Biochemical Characterization of WbpP, a New UDP-GlcNAc C4 Epimerase from *Pseudomonas aeruginosa* Serotype O6, *J. Bio. Chem*. 275(25):19060-19067 (Mar. 15, 2000).

Cunnion et al. 2001. Capsule production and growth phase influence binding of complement to *Staphylococcus aureus*. Infect Immun 69:6796-6803.

Datsenko, K. A., and B. L. Wanner. 2000. One-step inactivation of chromosomal genes in *Escherichia coli* K-12 using PCR products. Proc Natl Acad Sci USA 97:6640-6645.

Dean, C. R., C. V. Franklund, J. D. Retief, M. J. Coyne, Jr., K. Hatano, D. J. Evans, G. B. Pier, and J. B. Goldberg. 1999. Characterization of the serogroup O11 O-antigen locus of *Pseudomonas aeruginosa* PA103. J Bacteriol 181:4275-84.

DeJonge, M., D. Burchfield, B. Bloom, M. Duenas, W. Walker, M. Polak, E. Jung, D. Millard, R. Schelonka, F. Eyal, A. Morris, B. Kapik, D. Roberson, K. Kesler, J. Patti, and S. Hetherington. 2007. Clinical trial of safety and efficacy of INH-A21 for the prevention of nosocomial staphylococcal bloodstream infection in premature infants. J Pediatr 151:260-265.e1.

Dunphy, P.J., et al., The Plurality of Long Chain Isoprenoid Alcohols (Polyprenols) From Natural Sources, Biochim. Biophys. Acta 136, pp. 136-147 (1967).

Expression Library Screening (Procaryotic) Using AP-Fusion Proteins (last visited Nov. 1, 2010) at http://www.protocol-online.org/cgi-bin/prot/view_cache.cgi?ID=2752.

Falt, I. et al., Construction of recombinant aroA salmonellae stably producing the *Shigella dysenteriae* serotype 1 O-antigen and structural characterization of the *Salmonella/Shigella* hybrid LPS, Microb. Pathog. 20(1):11-30 (1996).

Faridmoayer, A. et al., Functional Characterization of Bacterial Oligosaccharyltransferases Involved in O-Linked Protein Glycosylation, *J. Bacteriol*. 189(22): 8088-8098 (Nov. 2007).

Fattom, A. I., J. Sarwar, A. Ortiz, and R. Naso. 1996. A *Staphylococcus aureus* capsular polysaccharide (CP) vaccine and CP-specific antibodies protect mice against bacterial challenge. Infect Immun 64:1659-65.

Fattom, A. I., J. Sarwar, L. Basham, S. Ennifar, and R. Naso. 1998. Antigenic determinants of S. aureus type 5 and type 8 capsular polysaccharide vaccines. Infect Immun 66:4588-92.

Fattom, A., R. Schneerson, S. C. Szu, W. F. Vann, J. Shiloach, W. W. Karakawa, and J. B. Robbins. 1990. Synthesis and immunologic properties in mice of vaccines composed of *Staphylococcus aureus* type 5 and type 8 capsular polysaccharides conjugated to *Pseudomonas aeruginosa* exotoxin A. Infect Immun 58:2367-74.

Feng et al., Structural and genetic characterization of the *Shigella bodyii* type 18 O antigen, Gene 355:79-86 (Aug. 2005).

Field, R.A., et al., Structural and Mechanistic Basis•of Bacterial Sugar Nucleotide-Modifying Enzymes, Biochemistry 42, pp. 7637-7647 (2003).

Foster, T. J. 2005. Immune evasion by *staphylococci*. Nature Reviews Microbiology 3:948-58.

Foster, T. J., and M. Hook. 1998. Surface protein adhesins of *Staphylococcus aureus*. Trends Microbiol 6:484-488.

Fridkin, S. K., J. C. Hageman, M. Morrison, L. T. Sanza, K. Como-Sabetti, J. A. Jernigan, K. Harriman, L. H. Harrison, R. Lynfield, and M. M. Farley. 2005. Methicillin-resistant *Staphylococcus aureus* disease in three communities. N Engl J Med 352:1436-44.

Gilbert, M., J. MacDonald, D. Gregson, J. Siushansian, K. Zhang, S. Elsayed, K. Laupland, T. Louie, K. Hope, M. Mulvey, J. Gillespie, D. Nielsen, V. Wheeler, M. Louie, A. Honish, G. Keays, and J. Conly. 2006. Outbreak in Alberta of community-acquired (USA300)

(56) References Cited

OTHER PUBLICATIONS methicillin-resistant *Staphylococcus aureus* in people with a history of drug use, homelessness or incarceration. Canad Med Assoc J 175:149-54.
Global Alliance for Vaccines and Immunization—Press releases (Mar. 11, 2006) at http://www.gavialliance.org/media_centre/press_releases/2006_03_09_en_pr_queenrania_delhi.php.
Glover, K. J., E. Weerapana and B. Imperiali. 2005. In vitro assembly of the undecaprenylpyrophosphate-linked heptasaccharide for prokaryotic N-linked glycosylation. Proc Natl Acad Sci U S A 102(40): 14255-14259.
GlycoVaxyn AG Appoints Renowned Vaccinologist Dr Stanley Plotkin to Supervisory Board, Press Release (Oct. 6, 2009) available at http://www.glycovaxyn.com/content/news/releases/09%/02010%/02006.pdf.
GlycoVaxyn AG Completes CHF 11.5 Million Series A Financing to Advance Novel Conjugated Vaccine Pipeline Towards Clinic, Press Release (Jul. 16, 2007) available at http://www.glycovaxyn.com/content/news/releases/06%2010%2019.pdf.
GlycoVaxyn AG Raises CHF 25 Million in Financing Led by Edmond de Rothschild Investment Partners, Press Release (Mar. 5, 2009) available at http://www.glycovaxyn.com/downloads/GlycoVaxyn%20Financing%20Release%2005-03- 09.pdf.
GlycoVaxyn and a Harvard University affiliated hospital receive USD 3.4 million NIH grant for *Staphylococcus aureus* vaccine development, Press Release (May 4, 2010) available at http://www.glycovaxyn.com/content/news/releases/10%/2005%2004.pdf.
GlycoVaxyn Appoints Philippe Dro as CEO, Press Release (May 20, 2008) available at http://www.sofinnova.fr/glycovaxyn-appoints-philippe-dro-as-ceo-actu-736.php.
GlycoVaxyn Opens to Partnerships; Series C Financing Round Planned for 2011, CEO Says, *mergermarket* pp. 1-2 (Nov. 25, 2009) at http://www.mergermarket.com/home/.
GlycoVaxyn Phase I Clinical Study Shows Positive Data with *Shigella dysenteriae* Vaccine Candidate (Oct. 8, 2010) available at http://www.glycovaxyn.com/content/news/releases/10%2010%/2008.pdf.
GlycoVaxyn Winner of the Life Sciences Prize 2006, Press Release (Oct. 19, 2006) available at http://www.glycovaxyn.com/content/news/releases/06%2010%2019.pdf.
GlycoVaxyn's First Clinical Study with Bioconjugate Vaccine Initiated, Press Release (Feb. 23, 2010) available at http://www.glycovaxyn.com/content/news/releases/10%2002%2023.pdf.
Goldberg, J. B., K. Hatano, G. S. Meluleni and G. B. Pier. 1992. Cloning and surface expression of *Pseudomonas aeruginosa* O antigen in *Escherichia coli*. Proc Natl Acad Sci U S A 89(22): 10716-20.
Gordon, H.T., et al., Rapid Paper Chromatography of Carbohydrates and Related Compounds, Anal. Chem. 28, pp. 849-855 (1956).
Gray, B.M. 1979. ELISA methodology for polysaccharide antigens: protein coupling of polysaccharides for adsorption to plastic tubes. J. Immunol. 28:187-192.
Guan, Z., et al., Extraction and identification by mass spectrometry of undecaprenyl diphosphate-MurNAc-pentapeptide-GlcNAc from *Escherichia coli*, Anal. Biochem. 345, pp. 336-339 (2005).
Guo, H., et al., Three UDP-hexose 4-epimerases with overlapping substrate specificity coexist in *E. coli* O86:B7, Biochem. Biophys. Res. Commun. 356, pp. 604-609 (2007).
Ho, M.M., et al., Preclinical laboratory evaluation of a bivalent *Staphylococcus aureus* saccharide-exotoxin A protein conjugate vaccine, Hum Vaccin, 2, 89-98, 2006.
Hoffmeister, D. et al., Two sequence elements of glycosyltransferases involved in urdamycin biosynthesis are responsible for substrate specificity and enzymatic activity, *Chem. & Bio.* 8: 557-567 (pub. online May 8, 2001).
Hofmann, K., et al., A Database of Membrane Spanning Protein Segments, Biol. Chem. Hoppe-Seyler 374, p. 166 (1993) (abstract).
Johnson, K., Synthesis of oligosaccharides by bacterial enzymes, *Glycoconjugate Journal* 16:141-146 (1999).

Jones, C. 2005. Revised structures for the capsular polysaccharides from *Staphylococcus aureus* types 5 and 8, components of novel glycoconjugate vaccines. Carbohydr Res 340:1097-106.
Josefsson, E., O. Hartford, L. O'Brien, J. M. Patti, and T. Foster. 2001. Protection against experimental *Staphylococcus aureus* arthritis by vaccination with clumping factor A, a novel virulence determinant. Journal of Infectious Diseases 184:1572-80.
Jursch, R., A. Hildebrand, G. Hobom, J. Tranum-Jensen, R.Ward, M. Kehoe and S. Bhakdi. 1994. Histidine residues near the N terminus of *staphylococcal* alpha-toxin as reporters of regions that are critical for oligomerization and pore formation. Infect Immun 62(6): 2249-56.
Kapitonov, D. & Yu, R.K., Conserved domains of glycosyltransferases, *Glycobio.* 9(10): 961-978 (1999).
Kazakova, S. V., J. C. Hageman, M. Matava, A. Srinivasan, L. Phelan, B. Garfinkel, T. Boo, S. McAllister, J. Anderson, B. Jensen, D. Dodson, D. Lonsway, L. K. McDougal, M. Arduino, V. J. Fraser, G. Killgore, F. C. Tenover, S. Cody, and D. B. Jernigan. 2005. A clone of methicillin-resistant *Staphylococcus aureus* among professional football players. N Engl J Med 352:468-75.
Kean, E.L., Separation of gluco- and galactocerebrosides by means of borate thin-layer chromatography, J. Lipid Res. 7, pp. 449-452 (1966).
King, M. D., B. J. Humphrey, Y. F. Wang, E. V. Kourbatova, S. M. Ray, and H. M. Blumberg. 2006. Emergence of community-acquired methicillin-resistant *Staphylococcus aureus* USA 300 clone as the predominant cause of skin and soft-tissue infections. Ann Intern Med 144:309-17.
Kiser, K. B., N. Bhasin, L. Deng and J. C. Lee. 1999. *Staphylococcus aureus* cap5P encodes a UDP-N-acetylglucosamine 2-epimerase with functional redundancy. J Bacteriol 181(16): 4818-24.
Klevens, R. M., M. A. Morrison, J. Nadle, S. Petit, K. Gershman, S. Ray, L. H. Harrison, R. Lynfield, G. Dumyati, J. M. Townes, A. S. Craig, E. R. Zell, G. E. Fosheim, L. K. McDougal, R. B. Carey, and S. K. Fridkin. 2007. Invasive methicillin-resistant *Staphylococcus aureus* infections in the United States. JAMA 298:1763-71.
Knirel, Y. A., V. V. Dashunin, A. S. Shashkov, N. K. Kochetkov, B. A. Dmitriev and I.L. Hofman. 1988. Somatic antigens of *Shigella*: structure of the O-specific polysaccharide chain of the *Shigella dysenteriae* type 7 lipopolysaccharide. Carbohydr Res 179: 51-60.
Kollef, M. H., A. Shorr, Y. P. Tabak, V. Gupta, L. Z. Liu, and R. S. Johannes. 2005. Epidemiology and outcomes of health-care-associated pneumonia: results from a large US database of culture-positive pneumonia. Chest 128:3854-3862.
Laemmli, U.K., Cleavage of Structural Proteins during the Assembly of the Head of Bacteriophage T4, Nature 227, pp. 680-685 (1970).
Law, D., Virulence factors of *Escherichia coli* O157 and other Shiga Toxin-producing *E. coli*, J. Appl. Microbiol. 88, pp. 729-745 (2000).
Lee, D. J., L. E. Bingle, K. Heurlier, M. J. Pallen, C. W. Penn, S. J. Busby and J. L. Hobman. 2009. Gene doctoring: a method for recombineering in laboratory and pathogenic *Escherichia coli* strains. BMC Microbiol 9: 252.
Lee, J. C., J. S. Park, S. E. Shepherd, V. Carey, and A. Fattom. 1997. Protective efficacy of antibodies to the *Staphylococcus aureus* type 5 capsular polysaccharide in a modified model of endocarditis in rats. Infect Immun 65:4146-51.
Lefebre, M.D., et al., Construction and Evaluation of Plasmid Vectors Optimized for Constitutive and Regulated Gene Expression in *Burkholderia cepacia* Complex Isolates, Appl. Environ. Microbiol. 68, pp. 5956-5964 (2002).
Liu, B., et al., Structure and genetics of *Shigella* O antigens, FEMS Microbiol. Rev. 32, pp. 627-653 (2008).
Lodish, et al., DNA Cloning with Plasmid Vectors, Molecular Cell Biology 7.1 (2000) available at http://www.ncbi.nim.nih.gov/bookshelf/br.fcgi?book=mcb&part=A1582.
Lodish, et al., Protein Glycosylation in the ER and Golgi Complex, Molecular Cell Biology 17.7 (2000) available at http://www.ncbi.nlm.nih.gov/bookshelf/br.fcgi?book=mcb&part=A4816.
Lowy, F. D. 1998. *Staphylococcus aureus* infections. New Engl J Med 339:520-32.
Marth, J.D. et al., Essentials of Glycobiology, Chapter 7 (Varki, et al. eds., 1999, Cold Spring Harbor, NY) available at: http://www.ncbi.nlm.nih.gov/bookshelf/br.fcgi?book=glyco&part=A465.

(56) References Cited

OTHER PUBLICATIONS

McDevitt, D., P. Francois, P. Vaudaux, and T. J. Foster. 1995. Identification of the ligand-binding domain of the surface-located fibrinogen receptor (clumping factor) of *Staphylococcus aureus*. Molecular Microbiology 16:895-907.

McDougal, L. K., C. D. Steward, G. E. Killgore, J. M. Chaitram, S. K. McAllister, and F. C. Tenover. 2003. Pulsed-field gel electrophoresis typing of oxacillin-resistant *Staphylococcus aureus* isolates from the United States: establishing a national database. J. Clin Microbiol 41:5113-20.

Meier-Dieter, U., R. Starman, K. Barr, H. Mayer, and P. D. Rick. 1990. Biosynthesis of enterobacterial common antigen in *Escherichia coli*. J Biol Chem 265:13490-13497.

Menzies, B. E., and D. S. Kernodle. 1996. Passive immunization with antiserum to a nontoxic alpha-toxin mutant from *Staphylococcus aureus* is protective in a murine model. Infect Immun 64:1839-41.

Merry, A. H., D. C. Neville, L. Royle, B. Matthews, D. J. Harvey, R. A. Dwek and P. M. Rudd. 2002. Recovery of intact 2-aminobenzamide-labeled O-glycans released from glycoproteins by hydrazinolysis. Anal Biochem 304(1): 91-99.

Messner, P., Bacterial glycoproteins, *Glycoconjugate Journal* 14:3-11 (1997).

Mikusova, K., et al., Decaprenylphosphoryl Arabinofuranose, the Donor of the D-Arabinofuranosyl Residues of Mycobacterial Arabinan, Is Formed via a Two-Step Epimerization of Decaprenylphosphoryl Ribose, J. Bacteriol. 187, pp. 8020-8025 (2005).

Moreillon, P., J. M. Entenza, P. Francioli, D. McDevitt, T. J. Foster, P. Francois, and P. Vaudaux. 1995. Role of *Staphylococcus aureus* coagulase and clumping factor in pathogenesis of experimental endocarditis. Infection & Immunity 63:4738-43.

Nanra, J. S., Y. Timofeyeva, S. M. Buitrago, B. R. Sellman, D. A. Dilts, P. Fink, L. Nunez, M. Hagen, Y. V. Matsuka, T. Mininni, D. Zhu, V. Pavliak, B. A. Green, K. U. Jansen, and A. S. Anderson. 2009. Heterogeneous in vivo expression of clumping factor A and capsular polysaccharide by *Staphylococcus aureus*: Implications for vaccine design. Vaccine 27:3276-80.

Nilsson of al. 1997. The role of staphylococcal polysaccharide microcapsule expression in septicemia and septic arthritis. Infect Immun 65:4216-4221.

O'Riordan, K. and J. C. Lee. 2004. *Staphylococcus aureus* capsular polysaccharides. Clin Microbiol Rev 17(1): 218-34.

Paton & Paton, Molecular Characterization of the Locus Encoding Biosynthesis of the Lipopolysaccharide O Antigen of *Escherichia coli* Serotype O113, *Infect. & Immun*. 67(11): 5930-5937 (Nov. 1999).

Pawlowski, A., G. Kallenius, and S. B. Svenson. 2000. Preparation of pneumococcal capsular polysaccharide-protein conjugate vaccines utilizing new fragmentation and conjugation technologies. Vaccine 18:1873-1885.

Perry, M.B., et al., Structure of the O-chain polysaccharide of the phenol-phase soluble lipopolysaccharide of *Escherichia coli* 0:157:H7[1], Biochem. Cell Biol. 64, pp. 21-28 (1986).

Qian, F., Y. Wu, O. Muratova, H. Zhou, G. Dobrescu, P. Duggan, L. Lynn, G. Song, Y. Zhang, K. Reiter, N. MacDonald, D. L. Narum, C. A. Long, L. H. Miller, A. Saul, and G. E. Mullen. 2007. Conjugating recombinant proteins to *Pseudomonas aeruginosa* ExoProtein A: A strategy for enhancing immunogenicity of malaria vaccine candidates. Vaccine 25:3923-3933.

Robbins, J. B., J. Kubler-Kielb, E. Vinogradov, C. Mocca, V. Pozsgay, J. Shiloach, and R. Schneerson. 2009. Synthesis, characterization, and immunogenicity in mice of *Shigella sonnei* O-specific oligosaccharide-core-protein conjugates. Proc Natl Acad Sci USA 106:7974-7978.

Royle, L., T. S. Mattu, E. Hart, J. I. Langridge, A. H. Merry, N. Murphy, D. J. Harvey, R. A. Dwek, P. M. Rudd. 2002. An analytical and structural database provides a strategy for sequencing O-glycans from microgram quantities of glycoproteins. Anal Biochem 304(1): 70-90.

Rubires, X., F. Saigi, N. Pique, N. Climent, S. Merino, S. Alberti, J. M. Tomas and M. Regue. 1997. A gene (wbbL) from *Serratia marcescens* N28b (O4) complements the rfb-50 mutation of *Escherichia coli* K-12 derivatives. J Bacteriol 179(23):7581-7586.

Rush, J. et al., A Novel Epimerase That Converts GlcNAc-P-P-undecaprenol to GalNAc-P-P-undecaprenol in *Escherichia coil* O157, *J. Bio. Chem* . 285(3): 1671-1680 (JBC Papers in Press, Nov. 18, 2009).

Rush, J.S., et al., Polyisoprenyl phosphate specificity of UDP-GlcNAc:undecaprenyl phosphate N-acetylglucosaminyl 1-P transferase from *E.coli*, Glycobiology 7, pp. 315-322 (1997).

Sambrook & Russell, Screening Bacterial Colonies by Hybridization: Small Numbers, *Cold Spring Harb. Protoc.*; 2006; doi:10.1101/pdb.prot3935 at http://cshprotocols.cshlp.org/cgi/content/full/2006/2/pdb.prot3935.

Samuel, G. et al., Biosynthesis of O-antigens: genes and pathways involved in nucleotide sugar precursor synthesis and O-antigen assembly, Carbohydr. Res. 338, pp. 2503-2519 (2003).

Sau, S., N. Bhasin, E. R. Wann, J. C. Lee, T. J. Foster and C. Y Lee. 1997. The *Staphylococcus aureus* allelic genetic loci for serotype 5 and 8 capsule expression contain the type-specific genes flanked by common genes. Microbiology 143: 2395-405.

Schaffer, A. C., and J. C. Lee. 2008. Vaccination and passive immunisation against *Staphylococcus aureus*. Int J Antimicrob Agents 32 Suppl 1:S71-S78.

Schwimmer, S., et al., Reagent for Differentiation of 1,4- and 1,6— Linked Glucosaccharides, Science 123, pp. 543-544 (1956).

Shorr, A. F. 2007. Epidemiology and economic impact of meticillin-resistant *Staphylococcus aureus* review and analysis of the literature. Pharmacoeconomics 25:751-68.

Spears, K., et al., A comparison of enterphathogenic and enterohaemorrahagic *Escherichia coli* pathogenesis, FEMS Microbiol. Lett. 255, pp. 187-202 (2006).

Spirig, U. et al., The *STT3* protein is a component of the yeast oligosaccharyltransferase complex, *Mol Gen Genet* 256:628-637 (1997).

Stenutz, R., et al., The structures of *Escherichia coli* O-polysaccharide antigens, FEMS Microbiol. Rev. 30, pp. 382-403 (2006).

Stephan, R., et al., First isolation and further characterization of enteropathogenic *Escherichia coli* (EPEC) O 157:H45 strains from cattle, BMC Microbiol. 4:10 (2004).

Stevenson, G., et al., Structure of the O Antigen of *Escherichia coli* K-12 and the Sequence of Its *rfb* Gene Cluster, J. Bacteriol. 176, pp. 4144-4156 (1994).

Sullam, P. M., A. S. Bayer, W. M. Foss, and A. L. Cheung. 1996. Diminished platelet binding in vitro by *Staphylococcus aureus* is associated with reduced virulence in a rabbit model of infective endocarditis. Infection & Immunity 64:4915-21.

Thakker, M., J.-S. Park, V. Carey, and J. C. Lee. 1998. *Staphylococcus aureus* serotype 5 capsular polysaccharide is antiphagocytic and enhances bacterial virulence in a murine bacteremia model. Infect Immun 66:5183-5189.

Tsai, C. M., and C. E. Frasch. 1982. A sensitive silver stain for detecting lipopolysaccharides in polyacrylamide gels. Anal Biochem 119:115-119.

Tuchscherr, L. P., F. R. Buzzola, L. P. Alvarez, J. C. Lee, and D. O. Sordelli. 2008. Antibodies to capsular polysaccharide and clumping factor A prevent mastitis and the emergence of unencapsulated and small-colony variants of *Staphylococcus aureus* in mice. Infect Immun 76:5738-44.

Unligil, U.M. & Rini, J.M., Glycosyltransferase structure and mechanism, *Curr. Op. Struct. Bio.* 10: 510-517 (2000).

Vanbleu, E. et al., Genetic and physical map of the pLAFR1 vector DNA Seq. 15(3):225-227 (2004).

Vaudaux, P. E., P. Francois, R. A. Proctor, D. McDevitt, T. J. Foster, R. M. Albrecht, D. P. Lew, H. Wabers, and S. L. Cooper. 1995. Use of adhesion-defective mutants of *Staphylococcus aureus* to define the role of specific plasma proteins in promoting bacterial adhesion to canine arteriovenous shunts. Infection & Immunity 63:585-90.

Vernachio, J., A. S. Bayer, T. Le, Y. L. Chai, B. Prater, A. Schneider, B. Ames, P. Syribeys, J. Robbins, J. M. Patti, J. Vemachio, A. S. Bayer, T. Le, Y.-L. Chai, B. Prater, A. Schneider, B. Ames, P. Syribeys, J. Robbins, and J. M. Patti. 2003. Anti-clumping factor A (56) References Cited

OTHER PUBLICATIONS immunoglobulin reduces the duration of methicillin-resistant *Staphylococcus aureus* bacteremia in an experimental model of infective endocarditis. Antimicrobial Agents & Chemotherapy 47:3400-3406.

Waechter, C.J., et al., Evidence for the Enzymatic Transfer of N-Acetylglucosamine from UDP-N-Acetylglucosamine into Dolichol Derivates and Glycoproteins by Calf Brain Membranes, Arch. Biochem. Biophys. 181, pp. 185-198 (1977).

Waechter, C.J., et al., Lipid Intermediates Involved in the Assembly of Membrane-Associated Glycoproteins in Calf Brain White Matter, Arch. Biochem. Biophys. 174, pp. 726-737 (1976).

Wang, L., et al., Organization of *Escherichia coli* O157 O Antigen Gene Cluster and Identification of Its Specific Genes, Infect. Immun. 66, pp. 3545-3551 (1998).

Wang, L., et al., The O-Antigen Gene Cluster of *Escherichia coli* O55:H7 and Identification of a New UDP-GlcNAc C4 Epimerase Gene, J. Bacteriol. 184, pp. 2620-2625 (2002).

Watts, A., D. Ke, Q. Wang, A. Pillay, A. Nicholson-Weller, and J. C. Lee. 2005. *Staphylococcus aureus* strains that express serotype 5 or serotype 8 capsular polysaccharides differ in virulence. Infect Immun 73:3502-11.

Whitfield, C., Biosynthesis and Assembly of Capsular Polysaccharides in *Escherichia coli*, Annu. Rev. Biochem. 75, pp. 39-68, (2006).

Wolfe, Reactions Adding Sugar Units to Proteins in the ER and Golgi Complex, Molecular and Cellular Biology, Wadsworth Publishing Co., CA, 873-75 (1993).

Zhang, L., et al., Molecular and chemical characterization of the lipopolysaccharide O-antigen and its role in the virulence of *Yersinia enterocolitica* serotype O:8, Mol. Microbiol. 23, pp. 63-76 (1997).

Zufferey, R. et al., *STT3*, a highly conserved protein required for yeast oligosaccharyl transferase activity in vivo, *The EMBO Journal*, 14 (20):4949-4960 (1995).

Apfel et al., 1999, "Use of genomics to identify bacterial undecaprenyl pyrophosphate synthetase: cloning, expression, and characterization of the essential uppS gene," Journal of Bacteriology 181(2):483-492.

Whitfield et al., 1995, "Biosynthesis of lipopolysaccharide O antigens," Trends in Microbiology 3(5):178-185.

Wright et al., 1967, "Characterization of a polyisoprenoid compound functional in O-antigen biosynthesis," PNAS USA 57:1798-1803.

Higashi et al., 1967, "Structure of a lipid intermediate in cell wall peptidoglycan synthesis: a derivative of a C55 isoprenoid alcohol," PNAS USA 57:1878-1884.

Benz & Schmidt 2002, "Never say never again: protein glycosylation in pathogenic bacteria," Molecular Microbiology 45:267-276.

Yoshida et al., 1999, "*Schizosaccharomyces pombe* stt3+ is a functional homologue of *Saccharomyces cerevisiae* STT3 which regulates oligosaccharyltransferase activity," Yeast, 15:497-505.

Hong et al., 1996, "Molecular cloning of a highly conserved mouse and human integral membrane protein (Itm1) and genetic mapping to mouse chromosome 9," Genomics 31:295-300.

Gutierrez et al., 2000, "Cloning of the *Entamoeba histolytica* STT3 Gene, a Subunit of the Oligosaccharyltransferase Complex," Arch. Med. Res., 4(suppl):S162-164.

Coutinho et al., 2003, "An evolving hierarchical family classification for glycosyltransferases," J. Mol. Biol. 328:307-317.

Swanson et al., 1991, "Evidence that the Major Outer Membrane Protein of *Chlamydia Trachomatis* is Glycosylated," Infection and Immunity 59(6):2120-2125.

Notice of Allowance issued in connection with U.S. Appl. No. 11/920,175; mailing date: Nov. 7, 2013.

\* cited by examiner

SYSTEM AND METHOD FOR THE PRODUCTION OF RECOMBINANT GLYCOSYLATED PROTEINS IN A PROKARYOTIC HOST

This application is a continuation of U.S. application Ser. No. 10/506,917, filed Sep. 3, 2004, which is a national stage application of PCT/CH03/00153, filed Mar. 5, 2003, which claims the benefit under 35 U.S.C. §119(e) of 60/364,655, filed Mar. 14, 2002, and which claims priority under 35 U.S.C. §119(a) to CH 2002 0394/02, filed Mar. 7, 2002. Each of the foregoing applications is incorporated by reference herein in its entirety.

FIELD OF INVENTION

The present invention relates to an expression system and a method for the production of recombinant human and/or animal and/or plant and/or prokaryotic and/or fungal glycoproteins. Such glycoproteins may serve as nutrition or medical drugs for human or animals or plants because of their identical structure to the glycoproteins normally produced in these organisms.

TECHNICAL BACKGROUND

Glycosylation constitutes one of the most important of all post-translational protein modifications in eukaryotic cells and may have numerous effects on function, structure, physical properties and targeting of particular proteins. Generally, the carbohydrate moiety is to be regarded as having significant effects on both the structure and on the physicochemical features of a protein and may affect its enzymatic activity, antigenicity or thermal stability. The sugars can be linked via the ε-amine group of an asparagine (N-glycosidic bond) or the hydroxyl group of a serine or threonine (O-glycosidic bond) residue.

The N-linked protein glycosylation Is by far the most common protein modification found in eukaryotes. The complex glycosylation process starts at the cytoplasmic face of the endoplasmatic reticulum (ER) with the assembly of an oligosaccharide on the lipid carrier dolichylpyrophosphate [Burda, P. and Aebi, M. (1999) The dolichol pathway of N-linked glycosylation. *Biochim Biophys Acta,* 1426, 239-257]: 2 N-acetylglucosamine and 5 mannose residues are attached to this lipid in a stepwise fashion. The lipid linked oligosaccharide (LLO) is then flipped into the lumen of the ER, where by addition of 4 mannose and 3 glucose residues full length LLO is obtained. In the central reaction of the process, this oligosaccharide is transferred to selected asparagine residues of newly synthesized polypeptides. This reaction is catalyzed by the oligosaccharyl transferase (OTase) in the lumen of the ER. The OTase Is a complex of at least 8 subunits and this enzyme is responsible for the formation of the N-glycosidic bond. While still in the ER, three glucose and one mannose residue are quickly removed from the oligosaccharide of the glycoprotein. Glycoproteins are then transported to the Golgi apparatus where further trimming and addition of sugar moieties occurs before they are targeted to their final destinations [Varki, A., Cummings, R., Esko, J., Freeze, H., Hart, G. and Marth, 3. (1999) *Essentials of Glycobiology.* Cold Spring Harbor Laboratory Press, Cold Spring Harbor, N.Y.]. Whereas the LLO synthesis is a highly conserved process in eukaryotic cells, the modifications in the Golgi are not only species specific but also cell-type specific and lead to a high degree of diversity with respect to the structure of the N-linked oligosaccharides.

PRIOR ART

The production of human proteins in a variety of heterologous expression systems has become an important technique to generate recombinant proteins for research purposes as well as pharmaceutical applications. It is generally recognized that there is no universal expression system available for production. Furthermore, the selection of a cell type for expression of heterologous proteins depends on many factors. These include criteria such as cell growth characteristics, expression levels, intracellular or extracellular expression, and biological activity of the protein of interest as well as its intended use. But one of the most important criteria to be considered is whether a protein needs to be glycosylated for its application. Many human therapeutics are glycoproteins, and the importance of the posttranslational modification of polypeptides with defined oligosaccharides is well documented by their implication in numerous biological phenomena.

In mammalian glycoproteins, the majority of N-glycans are of the complex type, i.e. they consist of a pentasaccharide core of two N-acetylglucosamine and three mannose residues. This core is the remaining structure of the oligosaccharide that was originally transferred from dolichylpyrophosphate to proteins. In the Golgi it is further modified with antennae comprising additional N-acetylglucosamine, galactose, sialic acid and often fucose residues. An enormous diversity of impressively complex oligosaccharide structures is thereby possible. The importance of the complex N-glycans and the essential role of these structures are shown with experiments using knock-out mice unable to synthesize these complex-type N-glycans. These mice die before birth. Recently the congenital disorder of glycosylation (CDG) has been described in humans. This is a group of congenital multi-systemic diseases characterized by deficiency in the generation of N-glycans. These disorders are manifested by a wide variety of clinical features, such as disorders of the nervous system development, psychomotor retardation, dysmorphic features, hypotonia, coagulation disorders, and immunodeficiency. The broad spectrum of features reflects the critical role of N-glycoproteins during embryonic development, differentiation, and maintenance of cell functions and emphasizes the importance of the correct oligosaccharide structure.

Since the majority of therapeutically relevant proteins are glycosylated in their natural forms, they should also be glycosylated as recombinant proteins in order to get the correct biological activity. Thus, monitoring of the glycosylation pattern in quality control of recombinant proteins to assure product safety, efficiency and consistency has become increasingly important. Systems for the expression of glycosylated proteins have been developed. The most commonly used are Chinese hamster ovary (CHO) cell lines [Grabenhorst, E., Schlenke, P., Pohl, S., Nlmtz, M. and Conradt, H. S. (1999) Genetic engineering of recombinant glycoproteins and the glycosylation pathway in mammalian host cells. *Glycoconjugate Journal,* 16, 81-97], insect cells [Altmann, F., Staudacher, E., Wilson, I. B. and Marz, L. (1999) Insect cells as hosts for the expression of recombinant glycoproteins. *Glycoconjugate Journal,* 16, 109-123] or fungal cells [Malissard, M., Zeng, S, and Berger, E. G. (1999) The yeast expression system for recombinant glycosyltransferases. *Glycoconjugate Journal,* 16, 125-139. or Maras, M., van Die, I., Contreras, R. and van den Hondel, C. A. (1999) Filamentous fungi as production organisms for glycoproteins of bio-medical interest. Glycoconjugate Journal, 16, 99-107]. These cell lines have all the capability to glycosylate proteins, but they exhibit major differences in the production of recombinant glycoproteins. As mentioned above, the synthesis of the LLO and the transfer of the oligosaccharide to polypeptides is a highly conserved mechanism in all eukaryotes, whereas further processing and trimming of the N-glycans in the Golgi vary between organisms and cell type. Therefore, the final structure of the recombinant glycoprotein is defined by the production cell used. CHO cells are the mammalian cell lines commonly used for the expression of recombinant glycoproteins. They are able to synthesize complex type N-glycans, but some human tissue-specific terminal sugar residues are not synthesized by these cells since they do not express the proper glycosyltransferases. Therefore, the host cell lines must be improved by genetic engineering with the introduction of these glycosyltransferases.

Insect cells [see also WO 00/52135] are also widely used to produce recombinant proteins, as they can synthesize large quantities of a protein of interest when infected with powerful baculovirus-based gene expression vectors, and they can provide post-translational modifications similar to those provided by mammalian cells. The N-glycosylation pathway parallels the mammalian pathway until the formation of the core pentasaccharide. But normally insect cells do not express additional transferases in the Golgi and therefore the N-glycans produced are truncated (paucimannosidic) instead of a complex type as found in mammalian cells.

Fungi, in particular *Saccharomyces cerevisiae* or *Pichia pastoris*, are suitable host organisms for the production of eukaryotic heterologous proteins. These systems combine well-known techniques for the molecular and genetic manipulations, the cells are easy to grow and they have the capability for complex post-translational modifications such as protein glycosylation. In contrast to animal cells, fungi do not further trim the oligosaccharide in the Golgi but instead elongate it directly by the addition of mannose residues to form mannanes with up to 200 mannose units. Some glycoproteins escape these modifications and their maturation is more limited, yielding short core type oligosaccharides with up to 13 mannose residues.

These three examples of N-glycosylation in eukaryotes emphasize the differences in the structure of N-glycans. The implication on the function reveals that exact analysis of the structure is essential. Significant advances in carbohydrate structural analyses have been achieved during the past years. Especially in mass spectrometry (on-line ESI-MS, nanospray tandem mass spectrometry (ESIMS/MS) and improved MALDI/TOF techniques), very sensitive instrumentation for glycosylation analysis has been made available.

Problems in Prior Art

The importance of a highly defined oligosaccharide structure on recombinant glycoproteins contrasts sharply to the inability of presently used biotechnological processes to generate glycoproteins. This is due to the fact that the structure of a protein-linked oligosaccharide is determined directly by the cell type used and all of the eukaryotic production systems exhibit this specificity. It might be possible to genetically engineer eukaryotic production cell lines in such a way that a defined oligosaccharide structure is produced. However, the plethora of glycosyltransferases active in the Golgi compartment of eukaryotes makes such an approach very difficult. Additional problems with the use of eukaryotic expression systems are the following: In general, the mammalian expression system has its drawbacks in the use of growth medium, which contains calf serum. This raises concern about biosafety because of possible contamination with bovine spongiform encephalopathy (BSE). Furthermore human cell line cultures are much more difficult to keep sterile, these cells grow slowly and require expensive process control. As mentioned before, the specific glycoprotein synthesized depends directly on the cell line or cell type used. In other words, a recombinant glycoprotein only gets modified with its original N-glycan if the heterologous system expresses the same enzymes of the N-glycosylation pathway as in its origin. Otherwise host cells must be adapted by genetic engineering of the glycosylation pathway in the Golgi (FIG. 1B), and this represents the major drawback of human cell lines in the expression of recombinant glycoproteins.

The difficulties of the production of recombinant proteins in insect cells with the help of the baculoviruses expression system are the following: Baculoviruses essentially have a lytic infection mode, i.e. when the product is harvested, a large proportion of the host cells is lysed and releases degradative enzymes. In addition, the protein synthesis is maximal near death of infected cells and it is possible that the overall processing of the protein is suboptimal at that time. Particularly proteins destined for the plasma membrane or for secretion are affected by the depletion of components of the post-translational machinery of the secretory pathway. Furthermore, large scale insect cell culture offers particular challenges to the biotechnologist due to the higher oxygen consumption and higher shear sensitivity of the cells as compared to mammalian cells. Like in mammalian cells, the major drawback in the heterologous expression of glycoproteins resides in the different structure of the N-glycan as described before. Especially the lack of terminal sialic acid residues is detrimental, because these sugars play important roles in glycoprotein biology.

To summarize, the three main eukaryotic expression systems mostly fail to produce glycans of a desired structure. In contrast to eukaryotic systems, the gram-negative bacterium *Escherichia coli* offers several technical advantages for the production of heterologous proteins. It is the oldest and most productive system used. However, the inability of *E. coli* cells to exert post-translational modifications of proteins remains the strongest drawback for its use as the preferred host for the production of human proteins.

SUMMARY OF THE INVENTION

To overcome the problem of production of recombinant glycoproteins in *E. coli*, a metabolic machinery capable to obtain protein glycosylation is introduced into this bacterium. It is therefore an object of the invention to provide an expression system with which recombinant proteins, in particular N-glycosylated proteins are producible.

This object of the invention is reached—according to a first aspect—by the combination of features of independent claim 1, wherein a system is proposed for the production of recombinant human, human-like, or animal, or plant, or fungal, or bacterial N-glycosylated target proteins, the system comprising a prokaryotic organism into which is introduced a genetic information encoding for a metabolic apparatus capable of carrying out the requested N-glycosylation of the target protein. The system according to the invention is characterized in that said prokaryotic organism also contains the genetic information required for the expression of one or more recombinant target proteins.

This object of the invention is reached—according to a second aspect—by the combination of features of independent claim 5, wherein a method is proposed for producing recombinant human, human-like, or animal, or plant, or fungal, or bacterial N-glycosylated target proteins, the system comprising a prokaryotic organism into which is introduced a genetic information encoding for a metabolic apparatus capable of carrying out the requested N-glycosylation of the target protein. The method according to the invention is characterized in that said prokaryotic organism also contains the genetic information required for the expression of one or more recombinant target proteins.

Additional and inventive features derive from the dependent claims.

Advantages over Prior Art

Since *E. coli* is easier to handle and to grow and its genetics are very well known, the production of human, human-like, animal or plant or fungal or bacterial glycoproteins in *E. coli* is a breakthrough in biotechnology.

As mentioned before, recombinant glycoproteins to date have to be produced in less suited eukaryotes. But although the first steps in the synthesis of N-glycoproteins are highly conserved in all organisms the further trimming and processing differs quite significantly between eukaryotes. Therefore the N-glycans of recombinant glycoproteins depend on the glycosylation genes present in the expression system used.

This could give rise to production of recombinant glycoproteins where the N-glycans differ in their structure compared to the original one.

In contrast, the introduction of a genetic information encoding for a metabolic apparatus capable of carrying out the requested glycosylation of the protein, e.g. an operon, into an organism that normally does not glycosylate proteins offers the opportunity to manipulate the structure of the N-glycan by introducing specific glycosyltransferases.

BRIEF DESCRIPTION OF THE DRAWINGS

Some of the problems known from prior art as well as the method according to the invention are explained in more detail referring to schematic drawings that are exemplary embodiments of the invention and are not intended to narrow the scope of protection of the present invention. There is shown in FIG. 1 the expression of recombinant glycoproteins in eukaryotes, whereas
FIG. 2 the *Escherichia coli* expression system, with the expression of a recombinant target protein and the introduction of a specific glycosylation pathway according to the invention; and in
FIG. 3 the legend for the signs representing individual elements of the oligosaccharides residues of the glycoproteins in FIG. 1 and FIG. 2.

DESCRIPTION OF THE INVENTION

Figure 1A:
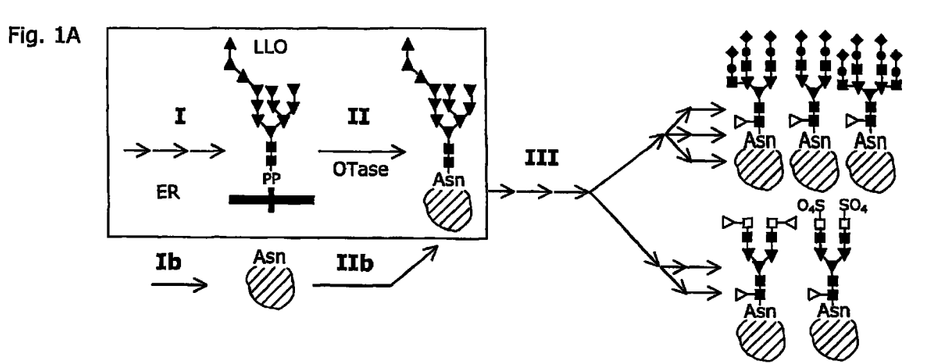
FIG. 1A shows the expression of a target glycoprotein.

FIG. 1 shows the expression of recombinant glycoproteins in eukaryotic expression systems. FIG. 1A shows the expression of a target glycoprotein, wherein the assembly of the lipid linked oligosaccharide (LLO; step I) and the transfer of the oligosaccharide to the protein by means of an OTase (step II) is a highly conserved process in the Endoplasmatic Reticulum (ER). In contrast, the modifications in the Golgi are cell type specific (step III).

FIG. 1B again shows the expression of a target glycoprotein, wherein the assembly of the lipid linked oligosaccharide (LLO; step I) and the transfer of the oligosaccharide to the protein by means of a OTase (step II) is a highly conserved process in the ER. In addition, an attempt to carry out genetic engineering of existing glycosylation pathways in the Golgi is shown. To produce a recombinant protein with a specific structure in eukaryotic cells, the host cells have to be adapted by genetic engineering of this glycosylatlon pathway in the Golgl. "X"-signs mark deletions required to exclude undesired pathways. "Asn" indicates an asparagine, "PP" a pyrophosphate, and "$SO_4$" a sulfate group.

Figure 1B:
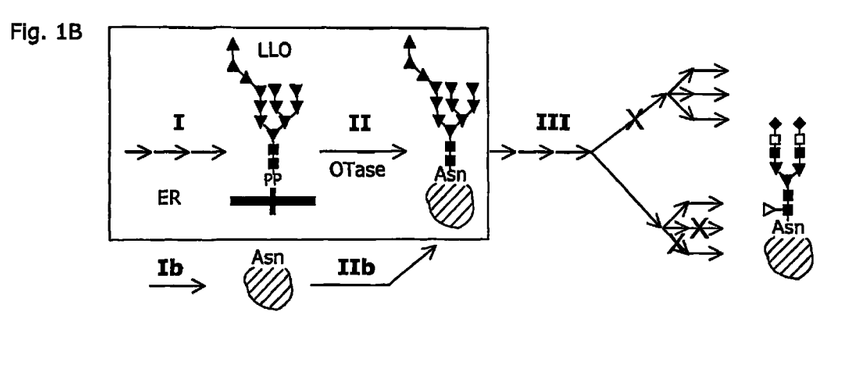
FIG. 1B shows genetic engineering of existing glycosylation pathways in the Golgi.

Both FIGS. 1A and 1B show that the expression of the recombinant protein is carried out outside the ER (step Ib) and that this target protein then is imported into the ER (step IIb). The explanation of the signs representing the individual elements of the oligosaccharides derives from the legend in FIG. 3.

Figures 2, 3:
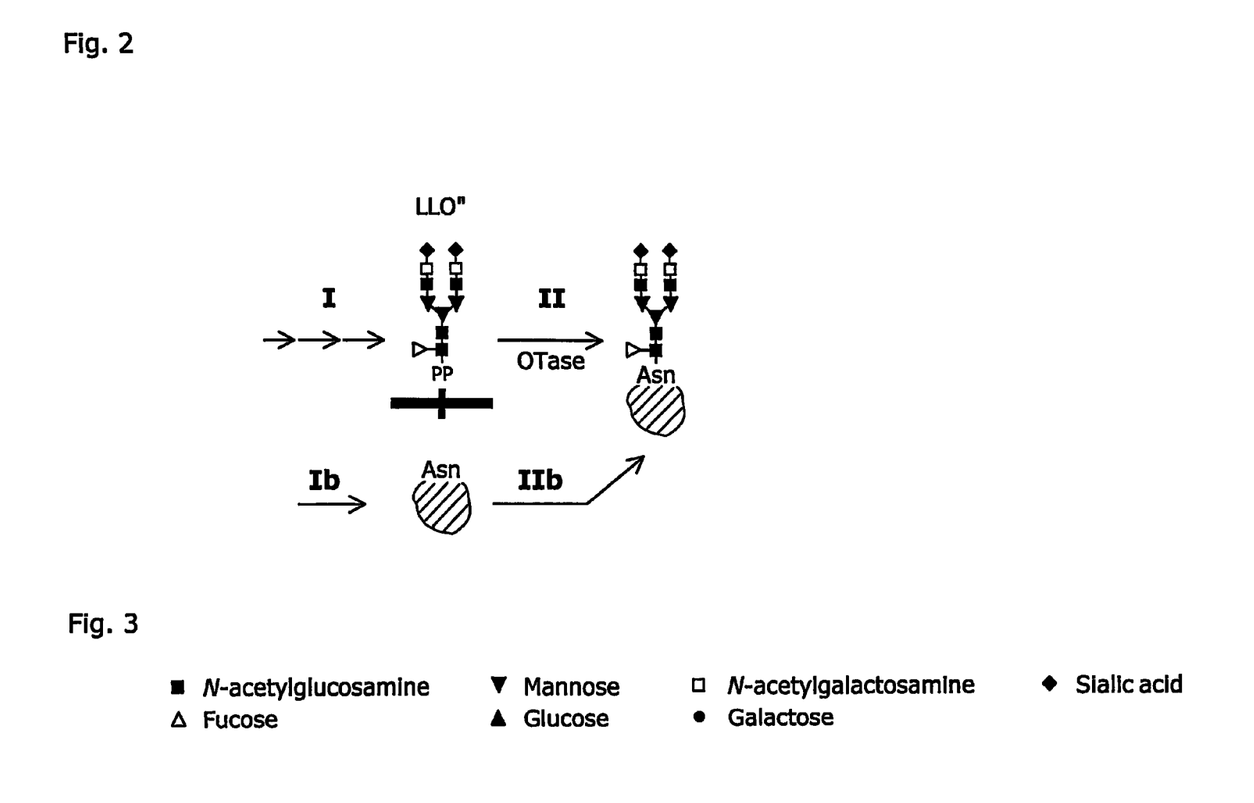

To obtain a recombinant glycoprotein with a specific oligosaccharide structure in eukaryotic cells requires the tailoring of highly complex, essential pathways and this might possibly interfere with the viability of the production cell. This is not the case in the *E. coli* system. Here, the tailoring is obtained by the introduction of specific components of the glycosylation machinery that lead to the desired glycoprotein (FIG. 2).

Since all the basic components (monosaccharides) required for the assembly of oligosaccharides are present in *E. coli* cells, the above mentioned solution requires the introduction:

a) of specific glycosyltransferases for the assembly of the oligosaccharide on a lipid carrier, and
b) an OTase that covalently links this oligosaccharide to specific residues of the desired protein.

This solution offers the possibility to design the oligosaccharide structure by the expression of specific glycosyltransferases and does not affect vital functions of the production cell.

FIG. 2 shows the *Escherichia coli* expression system according to the invention with the expression of a recombinant target protein (step Ib), which then is introduced to the glycoprotein synthesis (step IIb). To obtain a specific glycoprotein in *E. coli*, specific glycosyltransferases for the assembly of the lipid-linked oligosaccharide (LLO"; step I) are introduced into the host. The OTase covalently links this oligosaccharide to specific residues of the desired protein (step II).

In another attempt, the oligosaccharide, that is attached to the desired protein as described in FIG. 2, can be exchanged using a different oligosaccharide as a substrate in a enzymatic reaction in vitro. It was shown that the immobilized endo-β-N-acetylglucosa mimidase (Endo-A) from *Arthrobacter protophormiae* could transfer an oligosaccharide to ribonuclease B that contained a covalently linked N-acetylglucosamine [Fujita, K., Tanaka, N., Sano, M., Kato, I., Asada, Y. and Takegawa, K. (2000) Synthesis of neoglycoenzymes with homgogenous N-linked oligosaccharides using immobilized endo-β-N-acetylglucosaminidase A. Biochemical and Biophysical Research Communications, 267, 134-138]. Thus the invention gives the possibility to produce a glycoprotein in *E. coli* and then, in a second step, to modify the oligosaccharide that is covalently linked to the protein by exchanging it with a different oligosaccharide of defined structure with the Immobilized Endo-A in vitro.

The invention encompasses the production of glycosylated glycoproteins. There are many benefits derived from the glycosylation of such target proteins. Such benefits include, but are not limited to, increased in vivo circulatory half life of a protein; increased yields of recombinant proteins; increased biological activity of the protein including, but not limited to, enzyme activity, receptor activity, binding capacity; altered antigenicity; Improved therapeutic properties; increased capacities as a vaccine or a diagnostic tool, and the like. Examples of mammalian glycoproteins that can be produced with this invention and that can serve as medicaments for humans, animals or plants, include but are not limited to, erythropoietin, transferrin, interferons, immunoglobulines, interleukins, plasminogen, and thyrotropin. Also prokaryotic and/or fungal glycoproteins can be produced with the invention and can serve as medicaments for humans, animals and plants, e.g. glycoproteins from *C. jejuni* and from fungi. Further applications for glycoproteins produced with this invention include, but are not limited to, industrial enzymes, functional food, cosmetics, packaging materials, and textiles.

EXAMPLE 1

The present invention bases on the finding, that *Campylobacter jejuni*, a gram-negative bacterium, produces glycoproteins. Utilizing methods known per se, we have introduced the *C. jejuni* gene encoding AcrA, a glycoprotein, into *E. coli*. This results in the expression of non-glycosylated AcrA protein (see FIG. 2, step Ib). Subsequently and again utilizing known methods, an operon of *C. jejuni* encoding a) specific glycosyltransferases and b) an OTase was introduced into *E. coli*. This resulted in the production of specifically glycosylated AcrA protein according to the invention (see FIG. 2, steps I and II), as verified—always using methods known to skilled persons—by the binding of a highly specific lectin and glycosylation specific antibodies to the heterologously produced AcrA protein [Michael Wacker et al. (2002) N-linked glycosylation in *Campylobacter jejuni* and its functional transfer into *E. coli* (SCIENCE, Vol 298: 1790-1793]. In addition, the structure of the oligosaccharide linked to AcrA was verified by mass spectroscopy. Next it was shown, that the oligosaccharide was only transferred to the ε-amino group of the asparagine within the consensus sequence Asn-X-Ser/Thr where X can be any amino acid except Pro [Gavel, Y. and Von Heijne, G. (1990). Sequence differences between glycosylated and non-glycosylated Asn-X-Thr/Ser acceptor sites: implications for protein engineering. *Protein Eng*, 3, 433-442]. When the consensus sequence was mutated, the oligosaccharide was not transferred to the protein anymore. Therefore, it was verified—always using methods known to skilled persons—that the OTase of *C. jejuni* recognized the same consensus sequence as the OTase of eukaryotes and archaea and transferred the oligosaccharide by the same proposed mechanism to the protein [Wacker, M., Linton, D., Hitchen, P. G., Nita-Lazar, M., Haslam, S. M., North, S. J., Panico, M., Morris, H. R., Dell, A., Wren, B. W. and Aebi, M. (2002). N-linked glycosylation in *Campylobacter jejuni* and its functional transfer into *E. coli. Science,* 298: 1790-1793].

Specific glycosyl transferases and oligosaccharyl transferases utilized to genetically modify *E. coli* can be of prokaryotic or eukaryotic origin as glycosyl transferases are ubiquiteous and oligosaccharyl transferases are known from archaea.

What is claimed is:

1. A host prokaryotic organism comprising:
   (a) a target protein having a consensus sequence Asn-X-Ser(Thr), wherein X can be any amino acid except Pro, and
   (b) an oligosaccharyl transferase, wherein the oligosaccharyl transferase is the oligosaccharyl transferase from *Campylobacter jejuni*,
   wherein the target protein and the oligosaccharyl transferase are heterologous to the host organism and wherein the target protein is glycosylated at the Asn residue of the consensus sequence.

2. The host prokaryotic organism of claim 1, wherein the host prokaryotic organism is *Escherichia coli*.

3. A prokaryotic expression system obtained by a process comprising introducing into a host prokaryotic organism nucleic acids encoding:
   (a) a target protein, having a consensus sequence Asn-X-Ser(Thr), wherein X can be any amino acid except Pro, and
   (b) an oligosaccharyl transferase, wherein the oligosaccharyl transferase is the oligosaccharyl transferase from *Campylobacter jejuni*,
   wherein the target protein and the oligosaccharyl transferase are heterologous to the host organism and wherein the target protein is glycosylated at the Asn residue of the consensus sequence.

4. The host prokaryotic organism of claim 1, wherein said target protein is a bacterial protein.

5. The host prokaryotic organism of claim 3, wherein said target protein is a bacterial protein.

6. The host prokaryotic organism of claim 1, wherein said host prokaryotic organism is *Escherichia coli* and wherein said target protein is a bacterial protein.

7. The host prokaryotic organism of claim 3, wherein said host prokaryotic organism is *Escherichia coli* and wherein said target protein is a bacterial protein.

\* \* \* \* \*